US00PP20961P2

(12) United States Plant Patent
van Opstal

(10) Patent No.: US PP20,961 P2
(45) Date of Patent: Apr. 27, 2010

(54) *ABELIA×GRANDIFLORA* PLANT NAMED 'ABELOPS'

(50) Latin Name: *Abelia×grandiflora*
Varietal Denomination: Abelops

(76) Inventor: Ronnie A. van Opstal, St. Willebrordusstraat 3, Zundert (NL) 4882 NM ( * ) Notice: Subject to any disclaimer, the term of this patent is extended or adjusted under 35 U.S.C. 154(b) by 0 days.

(21) Appl. No.: 12/380,332

(22) Filed: Feb. 26, 2009

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

European Plant Breeder's Rights Application No. 2008/2108 filed Sep. 25, 2008 http://www.cpvoextranet.cpvo.europa.eu.

*Primary Examiner*—Susan B McCormick Ewoldt
(74) *Attorney, Agent, or Firm*—Audrey Charles

(57) ABSTRACT

A new and distinct cultivar of *Abelia* plant named 'Abelops', characterized by light purple-colored flowers, dark and light yellow-green variegated foliage edged with red-orange, deep purple-colored stems, and spreading to broadly upright, moderately vigorous growth habit, is disclosed.

1 Drawing Sheet

Latin name of genus and species of plant claimed: *Abelia×grandiflora.*

Variety denomination: 'Abelops'.

BACKGROUND OF THE INVENTION

The present invention relates to a new and distinct cultivar of *Abelia* plant botanically known as *Abelia×grandiflora* and hereinafter referred to by the cultivar name 'Abelops'. 'Abelops' is an ornamental flowering shrub grown for landscape and container use.

The new *Abelia* cultivar is a naturally-occurring sport of *Abelia×grandiflora* 'Little Richard', not patented, characterized by its non-variegated foliage and spreading to broadly upright, moderately vigorous growth habit. The new cultivar was discovered as a branch mutation and selected during May 2007 in a controlled outdoor nursery environment in Zundart, The Netherlands.

Asexual reproduction of the new cultivar by softwood stem cuttings since June 2007 in Zundart, The Netherlands has demonstrated that the new cultivar reproduces true to type with all of the characteristics, as herein described, firmly fixed and retained through successive generations of such asexual propagation.

SUMMARY OF THE INVENTION

The following are the most outstanding and distinguishing characteristics of this new cultivar when grown under normal horticultural practices in Zundart, The Netherlands:

1. Light purple-colored flowers;
2. Dark and light yellow-green variegated foliage edged with red-orange;
3. Deep purple-colored stems; and
4. Spreading to broadly upright, moderately vigorous growth habit.

Plants of the new cultivar differ from plants of the parent 'Little Richard' primarily in foliage color. The parent has non-variegated foliage.

Of the many commercially available *Abelia* cultivars, the most similar in comparison to the new cultivar is 'Kaleidoscope', U.S. Plant Pat. No. 16,988. However, in side by side comparisons in Zundart, The Netherlands, plants of the new cultivar 'Abelops' differ from plants of 'Kaleidoscope' by having a different leaf color, smaller leaves, and slightly different flower color.

In addition, plants of the new cultivar 'Abelops' are similar to 'Conti', U.S. Plant Pat. No. 8,472. However, in side by side comparisons in Zundart, The Netherlands, plants of the new cultivar 'Abelops' differ from plants of 'Conti' by having a different leaf color, larger flowers, and a different flower color.

BRIEF DESCRIPTION OF THE PHOTOGRAPHS

The accompanying photographs show, as nearly true as it is reasonably possible to make the same in color illustrations of this type, typical fall flower and foliage characteristics of the new cultivar. Colors in the photographs differ slightly from the color values cited in the detailed description, which accurately describes the colors of 'Abelops'. The plants were grown for approximately 1 year in a 2-liter container in Zundart, The Netherlands in an outdoor nursery location.

DETAILED BOTANICAL DESCRIPTION

Figure 1:
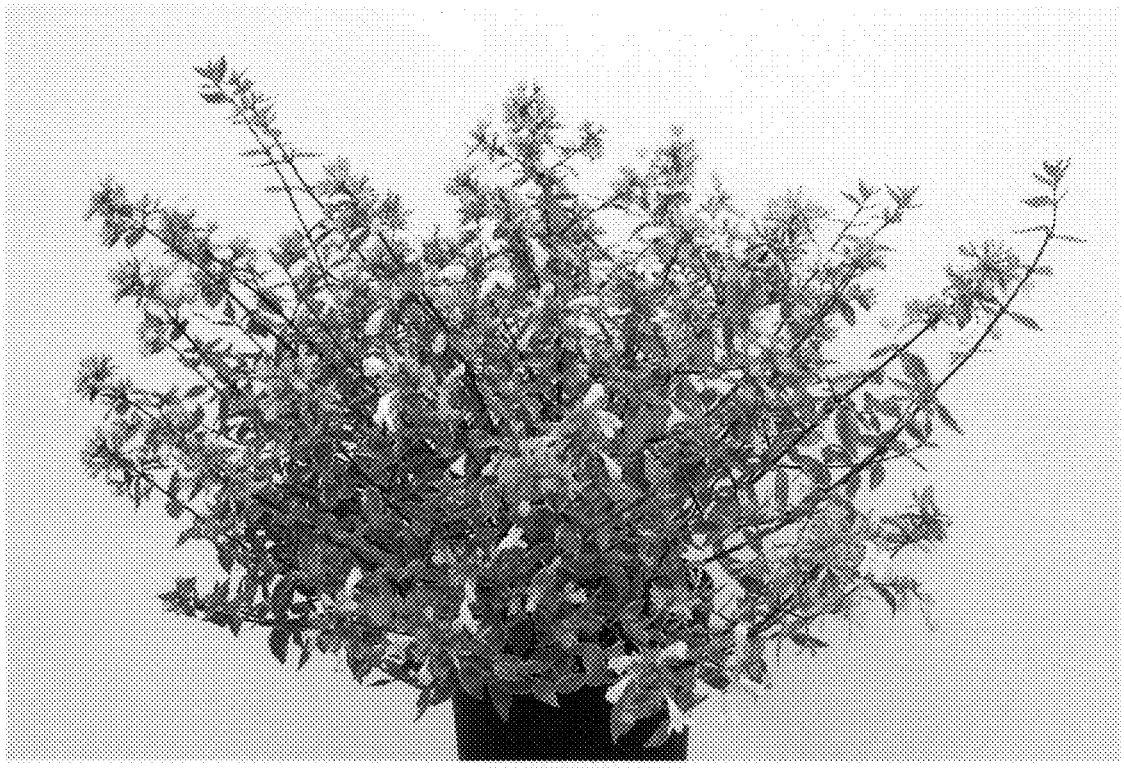
FIG. 1 illustrates a side view of the overall growth and flowering habit of 'Abelops'.
Figure 2:
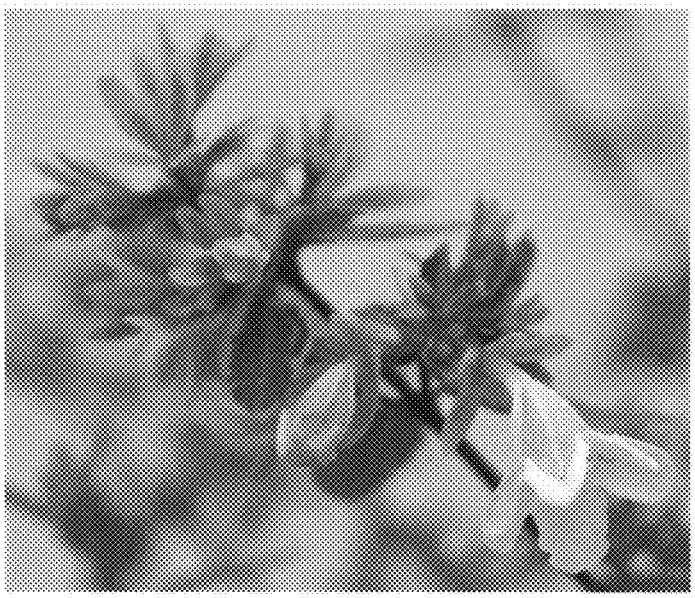
FIG. 2 illustrates a close-up view of an inflorescence of 'Abelops'.
Figure 3:
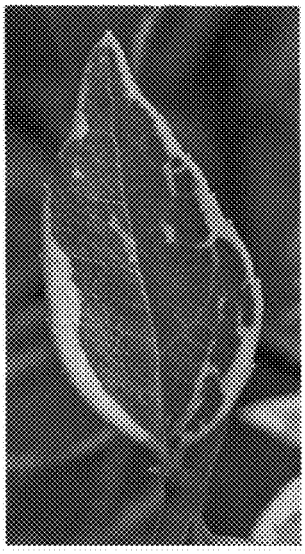
FIG. 3 illustrates a close-up view of a leaf of 'Abelops'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The data which define these characteristics were collected from asexual reproductions carried out in Zundart, The Netherlands. The plant history was taken in September on 1-year-old plants which were planted and grown in 2-liter containers in an outdoor nursery environment with daytime temperatures between 12° C. and 32° C. and nighttime temperatures between 4° C. and 14° C. No pinching, growth retardants or photoperiodic treatments were used. Observations were made when the plants were in natural daylight conditions.

Botanical classification: *Abelia×grandiflora* cultivar 'Abelops'.

Parentage:

*Parent.*—Branch mutation of *Abelia×grandiflora* 'Little Richard', not patented.

Propagation:

*Type cutting.*—Softwood stem.

*Time to initiate roots in summer.*—3 weeks with approximate temperatures of 20° C. day/14° C. night.

*Time to initiate roots in winter.*—4 weeks with approximate temperatures of 12° C. day/8° C. night.

*Time to produce a rooted young plant in summer.*—3 months with approximate temperatures of 20° C. day/14° C. night.

*Time to produce a rooted young plant in winter.*—3 months with approximate temperatures of 12° C. day/8° C. night.

*Root description.*—White, dense, thin, fibrous.

*Rooting habit.*—Freely branching.

Plant description:

*Type.*—Perennial. Overall shape: Flattened globular. High temperature tolerance: Tolerant to at least 35° C. Low temperature tolerance: Hardy to at least USDA Zone 7a.

*Commercial crop time.*—Approximately 12 months from rooted cutting to finish in a 13 cm container.

*Growth habit and general appearance.*—Spreading to broadly upright, moderately vigorous.

*Size.*—Height from soil level to top of plant plane: Approximately 27.6 cm. Width: Approximately 48.0 cm. Rate of growth: Moderate.

*Branching habit.*—Freely basal branching; pinching will improve basal branching. Quantity of main branches per plant: Approximately 30.

*Stem.*—Shape: Rounded. Strength: Very strong. Length: Approximately 27.9 cm. Diameter: Approximately 2.0 mm. Length of central internode: Approximately 2.2 cm. Texture: Moderately glossy, densely pubescent with very short, greyed white-colored hairs. Color: 187A to 187B transitioning with age to 170A.

Foliage description:

*General description.*—Quantity of leaves per unbranched lateral stem: Approximately 26. Quantity of leaves per branched lateral stem: Approximately 170. Form: Simple. Arrangement: Opposite. Durability to stress: Moderate to high.

*Leaves.*—Shape: Ovate. Margin: Serrate. Apex: Acute. Base: Rounded. Venation pattern: Pinnate. Length of mature leaf: Approximately 2.5 cm. Width of mature leaf: Approximately 1.2 cm. Texture of upper and lower surfaces: Smooth, glaborous, glossy. Color of upper surface of young (spring) foliage: Between 148A and 152A with an irregular margin of 34B and venation of 145A. Color of lower surface of young (spring) foliage: 147C with an irregular margin of 34C to 34D and venation of 145A. Color of upper surface of mature (fall) foliage: 146A with an irregular margin of 154A to 154C that is edged in 34C to 34D and with venation of 145A. Color of lower surface of mature (fall) foliage: 138B to 144B with an irregular margin of 150B to 150C that is edged in 34D and with venation of 145A.

*Petiole.*—Shape: Rounded, slightly curved. Length: Approximately 3.0 mm. Width: Approximately 1.0 mm. Color: 154A margined with 34C to 34D.

Flowering description:

*Flowering habit.*—Freely flowering under outdoor growing conditions with substantially continuous blooming from late summer through autumn.

*Lastingness of flower on the plant.*—Approximately 5 days.

Inflorescence description:

*General description.*—Type: Terminal compound cymes, self-cleaning with a persistent calyx. Quantity of flowers per lateral stem: Approximately 2. Fragrance: Very faint. Height: Approximately 5.0 cm. Width: Approximately 4.8 cm. Quantity of flowers and buds per inflorescence: Approximately 27. Rate of flower opening: Approximately 2 at a time per lateral branch.

*Peduncle.*—Strength: Strong. Aspect: Erect with secondary peduncles at an average angle of 40°. Length: Approximately 3.4 cm. Diameter: Approximately 1.5 mm. Texture: Smooth, glabrous. Color: 187A to 187B.

Flower description:

*General description.*—Type: Single, campanulate. Aspect: Outward to slightly drooping.

*Bud.*—Quantity per lateral stem: Approximately 25. Shape: Obovate, curved downward. Length: Approximately 1.6 cm. Diameter: Approximately 6.0 mm. Color: 76A with a base and lower surface of 76C to 76D. Rate of opening from this stage: Approximately 3 days.

*Corolla.*—Depth: Approximately 2.3 cm. Diameter: Approximately 1.7 cm.

*Petals.*—Quantity: 5, fused into an irregular campanulate shape. Appearance: Slightly glossy. Shape: Narrow oblong. Margin: Entire. Apex: Obtuse. Length: Approximately 2.1 cm. Width of two upper petals: Approximately 4.0 mm. Width of three lower petals: Approximately 5.0 mm. Texture of upper and lower surfaces: Smooth. Color of upper surface of two upper petals when first and fully open: 76A to 76B with 76D at tip and base. Color of lower surface of two upper petals when first and fully open: 76B with 76D at tip and base. Color of upper surface of three lower petals when first and fully open: 76D with N155A at tip and base. Color of lower surface of three lower petals when first and fully open: 76D with N155A at tip and base.

*Calyx.*—Shape: Rotate. Length: Approximately 7.0 mm. Diameter: Approximately 1.3 cm.

*Sepals.*—Quantity: 5. Arrangement: Rotate. Appearance: Slightly glossy. Shape: Narrow oval. Margin: Entire. Apex: Obtuse. Base: Cuneate. Length: Approximately 9.0 mm. Width: Approximately 2.5 mm. Texture of upper and lower surfaces: Smooth.

Color of upper and lower surfaces of immature sepals: 179C. Color of upper and lower surfaces of mature sepals: 174C to 174D.

*Pedicel.*—Strength: Strong. Aspect: Erect with secondary pedicels at an average angle of 40°. Length: Approximately 1.0 mm. Diameter: Approximately 0.5 mm. Texture: Smooth, glabrous. Color: 145A, upper surface tinged with 42B.

*Reproductive organs.*—Androecium: Stamen quantity: 4 per flower. Anther shape: Narrow oblong, basifixed. Anther length: Approximately 1.5 mm. Filament length: Approximately 1.4 cm. Anther color: N200D. Filament color: N155A. Pollen amount: Moderate. Pollen color: 155D. Gynoecium: Pistil quantity: 1 per flower. Pistil length: Approximately 1.8 cm. Stigma shape: Club. Stigma color: N155A. Style length: Approximately 1.75 cm. Style color: N155A. Ovary color: 146A to 146B.

Seed and fruit production: Neither seed nor fruit production has been observed.

Disease and pest resistance: No particular resistance or susceptibility to diseases or insects noted to date.

What is claimed is:

1. A new and distinct cultivar of *Abelia* plant named 'Abelops', substantially as herein shown and described.

* * * * *